US007193290B2

(12) United States Patent
Benzel et al.

(10) Patent No.: US 7,193,290 B2
(45) Date of Patent: Mar. 20, 2007

(54) SEMICONDUCTOR COMPONENT AND A METHOD FOR PRODUCING THE SAME

(75) Inventors: Hubert Benzel, Pliezhausen (DE); Heribert Weber, Nuertingen (DE); Frank Schaefer, Tuebingen (DE)

(73) Assignee: Robert Bosch GmbH, Stuttgart (DE)

( * ) Notice: Subject to any disclaimer, the term of this patent is extended or adjusted under 35 U.S.C. 154(b) by 48 days.

(21) Appl. No.: 10/479,563

(22) PCT Filed: Jul. 6, 2002

(86) PCT No.: PCT/DE02/02481

§ 371 (c)(1), (2), (4) Date: Dec. 3, 2003

(87) PCT Pub. No.: WO03/009334

PCT Pub. Date: Jan. 30, 2003

(65) Prior Publication Data

US 2004/0155751 A1 Aug. 12, 2004

(30) Foreign Application Priority Data

Jul. 18, 2001 (DE) ................................ 101 34 938

(51) Int. Cl.
*H01L 31/058* (2006.01)

(52) U.S. Cl. ...................... 257/467; 257/414; 438/700; 438/745

(58) Field of Classification Search ................ 257/414, 257/467, 532; 438/700, 745; 338/35; 216/2
See application file for complete search history.

(56) References Cited

U.S. PATENT DOCUMENTS 4,057,823 A 11/1977 Burkhardt et al.
4,144,636 A * 3/1979 Burkhardt et al. ............ 438/49
4,277,742 A * 7/1981 Kovac et al. ............... 324/689
4,347,550 A 8/1982 Rockliff
4,356,150 A * 10/1982 Johnson et al. ............... 422/98
4,795,968 A * 1/1989 Madou et al. ................ 422/88
5,332,697 A * 7/1994 Smith et al. ................ 438/479
5,629,474 A * 5/1997 Williams .................... 73/23.2
6,202,471 B1 * 3/2001 Yadav et al. ............... 73/31.05

* cited by examiner

*Primary Examiner*—Leonardo Andujar
*Assistant Examiner*—Victor A. Mandala, Jr.
(74) *Attorney, Agent, or Firm*—Kenyon & Kenyon LLP

(57) ABSTRACT

A semiconductor component, such as a humidity sensor, which has a semiconductor substrate, such as, for example, made of silicon, a first electrode and a second electrode and at least one first layer that is accessible for a medium acting from the outside on the semiconductor component, the first layer being arranged at least partially between the first and the second electrode. To reduce the costs for producing the semiconductor component the first layer has pores into which the medium reaches at least partially.

17 Claims, 3 Drawing Sheets

SEMICONDUCTOR COMPONENT AND A METHOD FOR PRODUCING THE SAME

FIELD OF THE INVENTION

The present invention relates to a semiconductor component, such as, for example, a humidity sensor, and a method for producing a semiconductor component.

BACKGROUND INFORMATION

Multi-layer semiconductor components for ascertaining the quantity and/or the type of a medium acting on the semiconductor component may have a capacitor arrangement. The medium may act on a layer located between a first and a second electrode. In the case of a semiconductor component which forms a humidity sensor, this may be the humidity in the air surrounding the semiconductor component. In a humidity sensor, atmospheric humidity may penetrate through a patterned top electrode into a moisture-sensitive layer and change the dielectric constant of this layer. This may lead to a moisture-dependent change in the capacitance of the capacitor formed by the two electrodes and the moisture-sensitive layer, which may be evaluated.

SUMMARY OF THE INVENTION

In contrast, a semiconductor component according to an exemplary embodiment of the present invention may have a layer which is provided with pores and may be produced inexpensively. The medium to be determined qualitatively and/or quantitatively may get into it, thereby changing the dielectric constant of the porous layer. Such a layer may be a silicon layer that is porous or is provided with pores. In contrast to other capacitive humidity sensors provided with a polymer layer, the porous layer of the semiconductor component according to an exemplary embodiment of the present invention may exhibit no moisture-dependent swelling.

With a semiconductor component according to an exemplary embodiment of the present invention, using such a porous layer, a sensor may be inexpensively produced both for a gaseous and for a liquid medium, which, in addition, may be characterized by a desired durability and reliability. The semiconductor component may be built as a sensor for determining the atmospheric humidity.

An exemplary method according to the present invention may produce the at least one porous layer of the semiconductor component according to the invention using one or more etching media containing hydrofluoric acid. The porosity in the starting layer of the semiconductor component of the present invention for producing the porous layer may be produced by applying an electric field between the upper side and the lower side of the semiconductor component, and an accompanying flow of electric current through the etching medium or the etching media. The porosity, i.e. particularly the relationship of the total extent of the hollow space of all pores to the volume of the remaining material of the layer may be adjusted in a simple, reproducible manner by applying a suitable electric voltage. In particular, the etching process may be stopped largely abruptly with the switch-off of the voltage. The production process may thereby be controlled in a desired manner.

According to an exemplary embodiment of the invention, the etching medium and/or the etching media for producing the pores may be hydrofluoric acid (HF) or a liquid mixture or a chemical compound which contains hydrofluoric acid.

In one exemplary embodiment of the invention, a highly volatile component, such as, for example, an alcohol such as ethanol, and/or purified water may be added to the etching medium(s) to dilute it/them.

Ethanol is believed to reduce the surface tension of an etching medium provided with it, thereby permitting better wetting of the silicon surface and a better penetration of the etching medium into etched pores. Moreover, the bubbles developing during the etching process may be smaller than without the addition of ethanol to the etching medium, and the bubbles may thus be able to escape better through the pores already formed.

According to an exemplary embodiment of the invention, the etching medium, the HF-concentration in the etching medium and/or the doping of the region to be etched and/or the temperature and possibly other process parameters of the etching method may be selected so that the etching process, i.e. the pore formation, may be adjusted in a suitable manner and/or may be stopped, that is, for example, largely abruptly, with the switch-off of the electric voltage.

DETAILED DESCRIPTION

Figure 1:
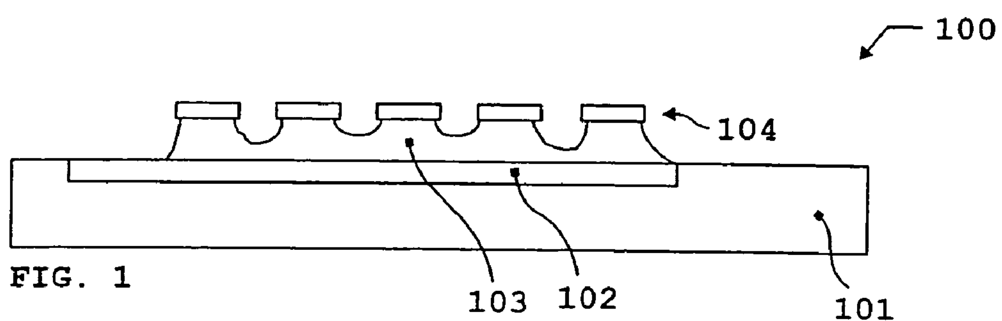
FIG. 1 shows a humidity sensor having a bottom electrode, a patterned top electrode and an overetched polymer layer located between both electrodes—in cross-section.

Humidity sensor 100, shown in FIG. 1, has a silicon substrate 101, a bottom electrode or lower electrode 102 formed by a suitably doped region in silicon substrate 101, an overetched polymer layer 103 and a patterned top electrode 104. Air reaches polymer layer 103 via the patterning or openings in patterned top electrode 104. The moisture contained in the air reaches polymer layer 103 and influences its dielectric constant. The dielectric constant of polymer layer 103 may be determined via lower electrode 102, polymer layer 103 and patterned top electrode 104 which form a plate-type capacitor. The instantaneous atmospheric humidity may be ascertained on the basis of the dielectric constant.

Changing atmospheric humidity may lead to shrinking or swelling of the polymer layer, which after some time may result in mechanical destruction of humidity sensor 100. In addition, the construction of the humidity sensor using a polymer may require considerable outlay and may therefore be costly for a mass-produced product, particularly in the automobile sector.

Figure 2:
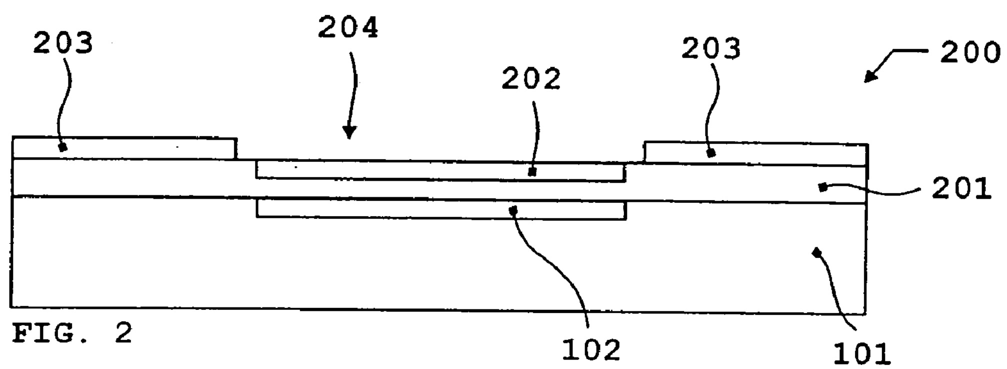
FIG. 2 shows the preliminary stage of a first exemplary embodiment of a humidity sensor according to the present invention—in cross-section.

Preliminary stage 200 of a first exemplary embodiment of a humidity sensor according to the present invention shown in FIG. 2 has a silicon substrate 101, a bottom electrode or lower electrode 102 formed by a doped region, a so-called intermediate layer 201 made of silicon deposited on the upper side of silicon substrate 101 and doped region 102, a top electrode or upper electrode 202 formed by a doped region, and a masking, formed by a mask layer 203, of the upper side of intermediate layer 201. The masking of the upper side of intermediate layer 201 is such that an etch opening 204 is formed above lower electrode 102, intermediate layer 201 and upper electrode 202. Preliminary stage 200 may be produced by a silicon semiconductor process.

To produce a perforated or porous top electrode 202 as well as a perforated or porous intermediate layer 201, in each case, for example, restricted to the region below etch opening 204, preliminary stage 200 shown in FIG. 2 may be put into an etching medium that, for example, contains hydrofluoric acid. An electric voltage is applied between the upper side of preliminary stage 200 and the lower side of preliminary stage 200. The electric voltage may cause current to flow in the etching medium which may produce pores or openings in top electrode 202 and subsequently in intermediate layer 201, in each case largely restricted to the region below etch opening 204. A result of the electrochemical etching using hydrofluoric acid is first further development 300, shown in FIG. 3, of the first exemplary embodiment shown in FIG. 2. The process parameters have been set during the etching so that the porosity of the relevant region of top electrode 202 and of relevant region 301 of intermediate layer 201 are substantially identical. Porosity is understood to be influenced by the relationship of cavity space or space accessible from the outside, which is given by the pores formed in the relevant regions, to the volume of the remaining material of the layer specific to a volumetric unit.

Production of a top electrode 202 whose porosity may be substantially the same as the porosity of intermediate layer 201, located below and next to it, in relevant regions 301, may be achieved according to the present invention in that the intensity of the current flowing through the etching medium when producing the pores in top electrode 202 and subsequently when producing the pores in intermediate layer 201 arranged below it is largely identical. If desired, when adjusting the current intensity for producing the porosity in top electrode 202, it may be required to be taken into account that region 202 is doped differently from intermediate layer 201. Given etching parameters which are otherwise constant, the depth of the porous etching may be predetermined by the period of time during which the electric current flows through the etching medium.

Figure 3:
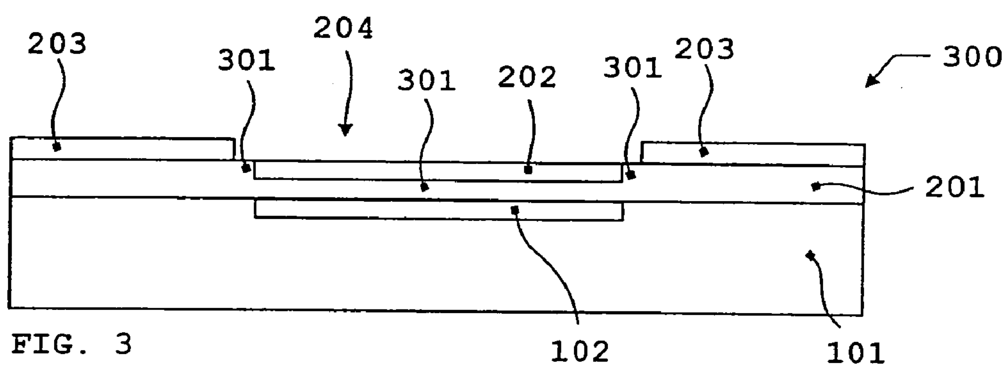
FIG. 3 shows a first further development of the first exemplary embodiment shown in FIG. 2—in cross-section.

The humidity sensor according to an exemplary embodiment of the present invention shown in FIG. 3 forms a capacitor having a porous, thin, upper electrode 202 and a porous region 301 in intermediate layer 201 between upper electrode 202 and lower electrode 102. Porous region 301 of intermediate layer 201 supports upper electrode 202. Humid air may get into porous region 301 of intermediate layer 201 through the fine pores of thin, upper electrode 202, relative to the thickness of intermediate layer 201. Therefore, the dielectric constant, and thus the evaluable capacitance between the upper and lower electrodes may change as a function of the specific atmospheric humidity.

The controlled utilization of the dependence of the form of the porosity on the doping may also be provided. For example, by using an n-doping for the upper electrode, one may obtain vertical pores, and by using a p-doping for the intermediate layer, one may obtain finely branched pores.

As will be explained in greater detail later in connection with FIG. 5, the two electrodes may be electrically connected via doped regions in the form of printed circuit traces to contact pads or contact areas, or to a circuit (not shown) integrated on the sensor. In addition, a reference capacitor may be produced on the sensor that, for example, is covered over the entire surface with metal during the subsequent metallization step. Alternatively, the covering may also be implemented by a passivation applied separately. In this manner, the reference capacitor may no be longer sensitive to moisture.

Figure 4:
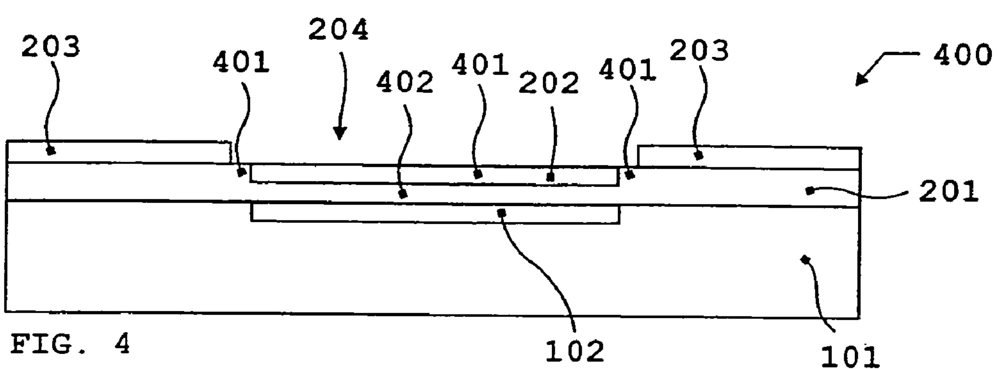
FIG. 4 shows a second further development of the first exemplary embodiment shown in FIG. 2—in cross-section.

FIG. 4 shows a second further development of the preliminary stage of a first exemplary embodiment shown in FIG. 2. In contrast to the first further development, shown in FIG. 3, of the preliminary stage of a first exemplary embodiment shown in FIG. 2, in region 401 of upper electrode 202 or of upper intermediate layer 201, the humidity sensor according to an exemplary embodiment of the present invention shown in FIG. 4 has a porosity which is perceptibly less than the porosity of intermediate layer 201 located below upper electrode 202. To achieve this, upper electrode 202, i.e. the corresponding doped region which forms the upper electrode, may be porously etched in a time-controlled manner by applying an electric voltage in hydrofluoric acid. In so doing, work may be performed using a low current density to cause a low porosity. After intermediate layer 201 has been porously etched in the region of upper electrode 202, the current density is markedly increased. The underlying intermediate layer is now likewise porously etched, but with a perceptibly higher porosity compared to the porosity of upper electrode 202. The porously etched regions are delimited laterally by mask layer 203. In contrast to the first further development, intermediate layer 201 is markedly more porous than the doped region or the doped layer which forms upper electrode 202, as already explained. The feature in this exemplary embodiment of the present invention is that the change in the dielectric constant in response to a change in the atmospheric humidity, which acts on the humidity sensor of the present invention, happens primarily—as desired—in intermediate layer 201 or in the intervening space between the upper and lower electrodes. Care may be required to be taken in the porous etching of the present invention that the porous residual material in the intervening space between the upper and lower electrodes is still stable enough that it provides sufficient mechanical support for the upper electrode.

Figure 5:
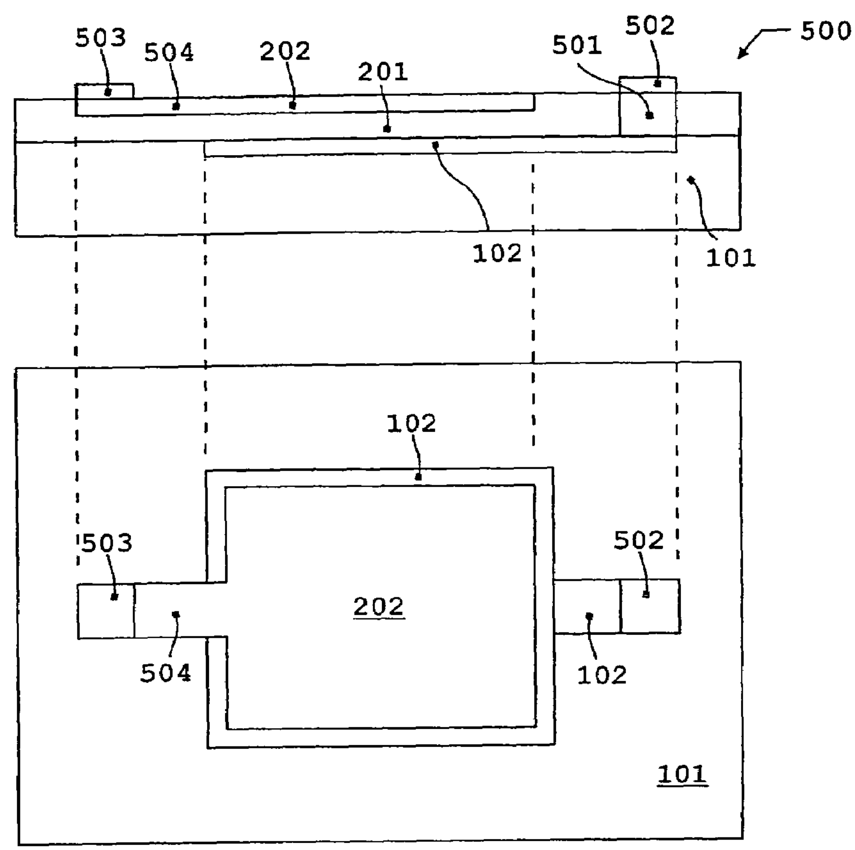
FIG. 5 shows an exemplary embodiment of a humidity sensor from FIG. 3 or 4, provided with electrical connections—in cross-section and in plan view.

FIG. 5 shows, in cross-section and in plan view, the exemplary embodiment of a humidity sensor 500 from FIG. 3 or 4, provided with electrical connections. Lower electrode 102 is connected via a suitable plated-through hole 501 to a contact area 502 for its external contacting. Upper electrode 202 is connected via a suitable contact deck 504 to a contact area 503 for its external contacting. The capacitance of the capacitor formed by upper electrode 202, lower electrode

102 and porous layer 301 or 402 located in between is determined via the external contactings. As already explained, the dielectric constant of the porous layer arranged between the two electrodes is a function of the specific medium which is able to penetrate from the outside into the pores of the porous layer. In the same manner, the dielectric constant of the porous layer is a function of the concentration of the medium in question. In the example of a humidity sensor described here, atmospheric humidity penetrates via porous upper electrode 202 into porous region 301 or 402, so that the capacitance of the capacitor changes. This change is supplied via contact areas 502 and 503 to an evaluation circuit (not shown) which ascertains or quantitatively determines the capacitance change and the changed atmospheric humidity giving rise to it. To this end, a reference capacitor may be used, for example, which is likewise integrated on the semiconductor component (not shown).

While the upper part of FIG. 5 shows humidity sensor 500 in cross-section, the lower part of FIG. 5 shows humidity sensor 500 in plan view. It may be inferred from the plan view of humidity sensor 500 that lower electrode 102 and upper electrode 202 have a rectangular outline, and are arranged in parallel, displaced in height relative to each other. Their outlines largely coincide.

Figure 6:
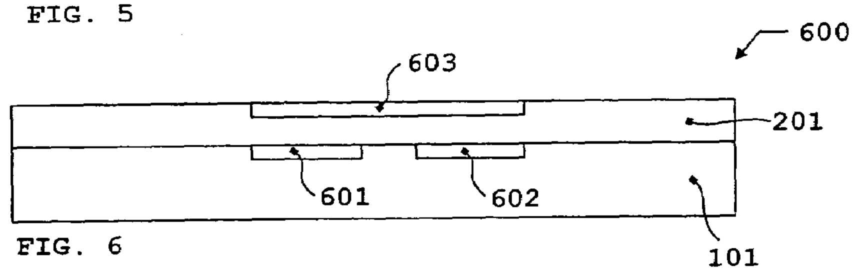
FIG. 6 shows a first variant of a second exemplary embodiment of a humidity sensor according to the present invention, having two electrodes arranged at the same level and a screening electrode located above them—in cross-section.

First variant 600 of a second exemplary embodiment of a humidity sensor according to the present invention shown in FIG. 6 has two electrodes 601 and 602 arranged at the same level. It may be inferable from the cross-section of the first variant, i.e. from semiconductor component 600 shown in FIG. 6 that first electrode 601 and second electrode 602 are covered by a screening electrode 603. Screening electrode 603, the region of intermediate layer 201 below screening electrode 603 and the region between first electrode 601 and second electrode 602 have been made porous in the manner described. In the example of a humidity sensor presented here, atmospheric humidity gets between first electrode 601 and second electrode 602 via the pores in screening electrode 603, the porous region (not shown) of intermediate layer 201 and the porous region (not shown) between electrodes 601 and 602. The dielectric constant of the porous region between first electrode 601 and second electrode 602 thereby changes, so therefore the capacitance of the described capacitor changes. The change in capacitance may be evaluated for the quantitative determination of the atmospheric humidity.

Figure 7:
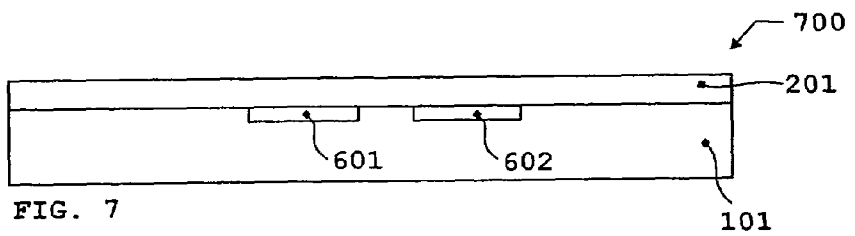
FIG. 7 shows the humidity sensor shown in FIG. 6 without screening electrode—in cross-section.

FIG. 7 shows the humidity sensor of the present invention depicted in FIG. 6 without screening electrode 603. Like the exemplary embodiment shown in FIG. 6, the exemplary embodiment of a semiconductor component 700 shown in FIG. 7 has an intermediate layer 201 that has been made porous by the aforesaid measures in the region of first electrode 601 and second electrode 602. In the same manner, the region between first electrode 601 and second electrode 602 of exemplary embodiment 700 in FIG. 7 is porous, so that atmospheric humidity acting from outside on semiconductor component 700 leads to a change in the dielectric constant of the layer between the two electrodes 601 and 602, which may be evaluated in the manner described for the quantitative ascertainment of the atmospheric humidity.

Figure 8:
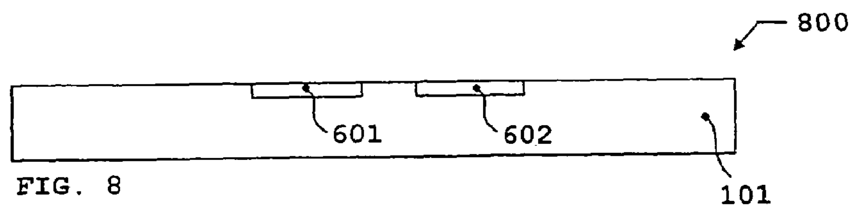
FIG. 8 shows the humidity sensor shown in FIG. 6 without screening electrode and without intermediate layer—in cross-section.

Humidity sensor 800 shown in FIG. 8 differs from the exemplary embodiment shown in FIG. 6, in that it has neither a screening electrode 603 (see FIG. 6) nor a porous intermediate layer 201 (see FIG. 7). Thus, humidity sensor 800 shown in FIG. 8 has only a silicon substrate 101 and two suitably doped regions which form first electrode 601 and second electrode 602. Humidity sensor 800 again has a porous region or a porous layer (not explicitly shown) between the two electrodes 601 and 602. In the same manner as for the semiconductor component shown in FIG. 6 and FIG. 7, atmospheric humidity acting on humidity sensor 800 from the outside gets between the two electrodes 601 and 602 and changes the dielectric constant of the porous layer arranged between the two electrodes. The accompanying change in capacitance may be detected for ascertaining the atmospheric humidity currently acting on the humidity sensor.

Figure 9:
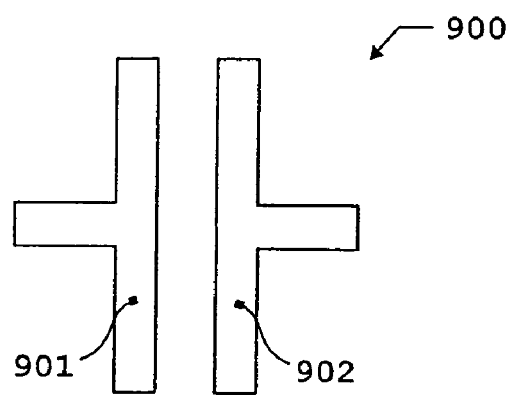
FIG. 9 shows a first exemplary embodiment for the bottom electrodes, shown in FIGS. 6 through 8, in the form of a plate-type capacitor—in plan view.

FIG. 9 shows a first exemplary embodiment 900 for the electrodes, shown in cross-section in FIGS. 6 through 8, which form a plate-type capacitor. Plate-type capacitor 900 has a first bottom electrode 901 and a second bottom electrode 902.

Figure 10:
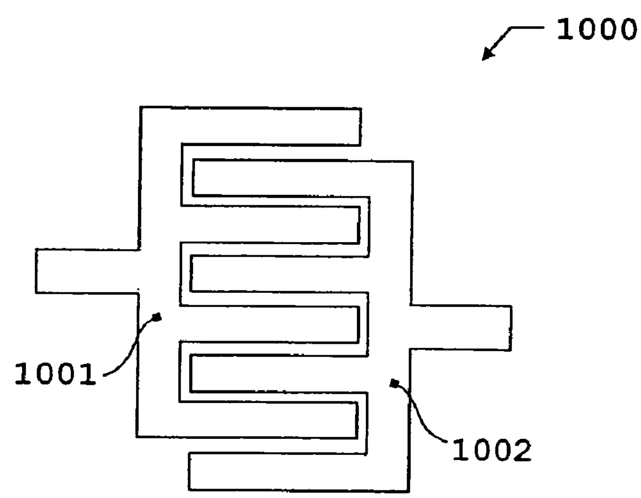
FIG. 10 shows a second exemplary embodiment for the bottom electrodes, shown in FIGS. 6 through 8, in the form of an interdigital structure formed by two intermeshing comb-type electrodes—in plan view.

FIG. 10 shows a second exemplary embodiment for the electrodes shown in cross-section in FIGS. 6 through 8. They have the form of two intermeshing comb-type electrodes 1001 and 1002 which form a so-called interdigital structure 1000.

Figure 11:
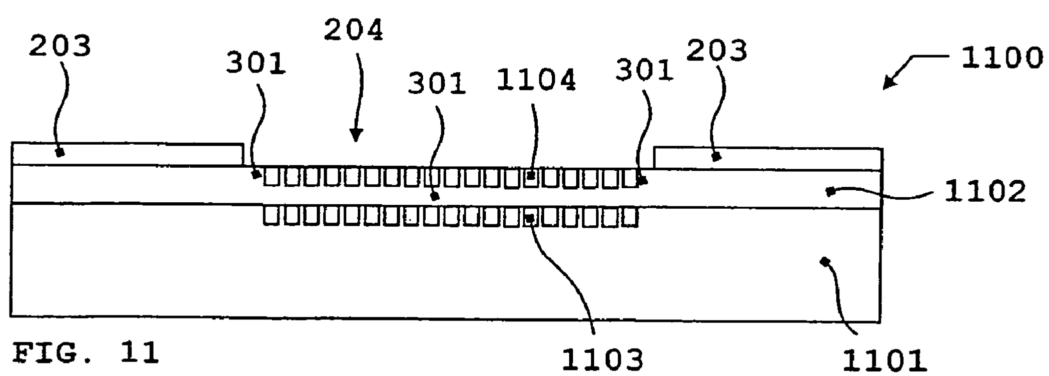
FIG. 11 shows another humidity sensor according to an exemplary embodiment of the present invention which has a reticular upper electrode and a reticular lower electrode—in cross-section.

FIG. 11 shows another humidity sensor 1100 according to the present invention—in cross-section. Silicon substrate 1101 and silicon intermediate layer 1102 of FIG. 11 have a suitable p-doping. On p-doped silicon substrate 1101, a—in plan view (not shown)—reticular or latticed lower electrode, which is designated by 1103 in the cross-sectional drawing, has been formed by an n-doped region, corresponding to this form, in silicon substrate 1101.

P-doped silicon intermediate layer 1102 has been deposited on silicon substrate 1101 and the n-doped region, i.e. lower electrode 1103. Silicon intermediate layer 1102 is likewise provided with an n-doping so that, in turn, an n-doped region is formed. The n-doped region in turn forms a—in plan view (not shown)—reticular or latticed upper electrode designated in the cross-sectional drawing of FIG. 11 by 1104. The production of the n-doped regions and the deposition of the intermediate layer may be carried out in known manner, so that it is not necessary to discuss it in greater detail.

To produce porous region 301 of FIG. 11, the structure of FIG. 11 described above is etched electrochemically in the manner already described. Because of the voltage difference between the upper side and the lower side of the structure shown in FIG. 11, during the etching process, an electric current flows which, starting from the etching medium surrounding the structure of FIG. 11, flows substantially uniformly through p-doped, epitactically deposited intermediate layer 1102, and flows past the n-doped electrodes without penetrating them. Expressed differently, the current density in the n-doped electrodes is largely negligible compared to the current density in intermediate layer 1102. The result is that, during the etching process, pores are formed almost exclusively in layer 1102 and not in latticed electrodes 1103 and 1104. That is to say, only intermediate layer 1102 is porous below etch opening 204 in the etch mask; in contrast, electrodes 1103 and 1104 are not, or are largely not porous. Porous region 301 in intermediate layer 1102 is then used in the manner already described for the quantitative and/or qualitative determination of the medium like, in particular, air which has penetrated from above into the intermediate layer. The moisture or water content of the air may be determined capacitively with the aid of the structure, shown in FIG. 11, which, in particular, is intended to form a humidity sensor according to an exemplary embodiment of the present invention. N-doped electrodes 1103 and 1104 of the present invention may be characterized in that they are not affected during the electrochemical etching. Therefore, their electric conductivity may be largely retained in spite of the etching process (no material removal). In addition, leakage currents may be substantially avoided by the use of n-doped electrodes in p-doped material such as, in particular, silicon.

The List of Reference Numerals is as follows: 100 known humidity sensor; 101 silicon substrate; 102 bottom electrode, lower electrode, formed by suitably doped region; 103 overetched polymer layer; 104 patterned top electrode, upper electrode; 200 preliminary stage of a first specific embodiment of a humidity sensor according to the present invention; 201 silicon intermediate layer; 202 top electrode, upper electrode, doped region; 203 mask layer; 204 etch opening; 300 first variant of the first specific embodiment shown in FIG. 2; 301 porous region in intermediate layer 201, which extends in the entire region below etch opening 204 up to bottom electrode 102; 400 second variant of the first specific embodiment shown in FIG. 2; 401 region having low porosity, which extends in the region below etch opening 204 up to approximately the lower side of top electrode 202; 402 region having great porosity, in relation to region 401, which extends in the region below etch opening 204 up to approximately the lower side of bottom electrode 102; 500 exemplary embodiment of a humidity sensor from FIG. 3 or 4, provided with electrical connections, in cross-section and in plan view; 501 plated-through hole; 502 contact area for contacting of the bottom electrode; 503 contact area for contacting of the top electrode; 504 contact deck for contacting of the top electrode; 600 first variant of a second specific embodiment of a humidity sensor according to the present invention, having two electrodes arranged at the same level and a screening electrode located above them; 601 first bottom electrode; 602 second bottom electrode; 603 screening electrode; 700 the humidity sensor of the present invention shown in FIG. 6 without screening electrode; 800 the humidity sensor of the present invention shown in FIG. 6 without screening electrode and without intermediate layer; 900 a first specific embodiment for the electrodes, shown in FIGS. 6 through 8, in the form of a plate-type capacitor; 901 first bottom electrode; 902 second bottom electrode; 1000 a second specific embodiment for the electrodes, shown in FIGS. 6 through 8, in the form of an interdigital structure formed by two intermeshing comb-type electrodes; 1001 first bottom electrode in the form of a comb; 1002 second bottom electrode in the form of a comb; 1100 example of a further specific embodiment of a humidity sensor according to the present invention having reticular or latticed electrodes; 1101 p-doped silicon substrate; 1102 p-doped silicon intermediate layer; 1103 reticular lower electrode; 1104 reticular upper electrode.

What is claimed is:

1. A semiconductor component, comprising:

a semiconductor substrate;

a first electrode;

a second electrode;

at least one first layer arranged at least partially between the first electrode and the second electrode, the first layer being accessible for a medium acting from an outside on the semiconductor component and having pores into which the medium is reachable at least partially, wherein at least one of the first electrode and the second electrode are formed at least partially by at least one of a suitably doped semiconductor layer and a metallic layer; and a second porous layer having a porosity is less than a porosity of a first porous layer, the second porous layer forming the first electrode, via which the medium one of completely and partially reaches the first porous layer.

2. The semiconductor component of claim 1, wherein the semiconductor component functions as a humidity sensor.

3. The semiconductor component of claim 1, wherein the semiconductor substrate includes silicon.

4. The semiconductor component of claim 1, wherein the medium is one of gaseous and liquid.

5. The semiconductor component of claim 1, wherein the medium includes air having humidity.

6. The semiconductor component of claim 1, wherein the porosity of the second porous layer is influenced by a relationship of a volume of pores to a material of the second porous layer.

7. The semiconductor component of claim 1, wherein the first and the second electrodes are arranged essentially on the same level with a distance to one another.

8. A semiconductor component, comprising:

a semiconductor substrate;

a first electrode;

a second electrode; and at least one first layer arranged at least partially between the first electrode and the second electrode, the first layer being accessible for a medium acting from an outside on the semiconductor component and having pores into which the medium is reachable at least partially, wherein at least one of the first electrode and the second electrode are formed at least partially by at least one of a suitably doped semiconductor layer and a metallic layer, wherein:

the first and the second electrodes are arranged essentially on the same level with a distance to one another, and the first and second electrodes form an interdigital structure.

9. A semiconductor component, comprising:

a semiconductor substrate;

a first electrode;

a second electrode;

at least one first layer arranged at least partially between the first electrode and the second electrode, the first layer being accessible for a medium acting from an outside on the semiconductor component and having pores into which the medium is reachable at least partially; and a third porous layer to at least one of cover and protect at least one of the first electrode, the second electrode, and a first porous layer, wherein the first and second electrodes form an interdigital structure.

10. A method for producing a semiconductor component, comprising:

forming, by an etching medium, at least one porous layer arranged at least partially between a first electrode and a second electrode of the semiconductor component so that the at least one porous layer is accessible for a medium acting from an outside on the semiconductor component and includes pores into which the medium is reachable at least partially, wherein the at least one porous layer is formed by applying an electric field between an upper side and a lower side of the semiconductor component and setting of electric current which flows through the etching medium.

11. The method of claim 10, wherein the etching medium includes one of hydrofluoric acid and HF acid.

12. The method of claim 10, further comprising:

providing the etching medium with at least one additive.

13. A method for producing a semiconductor component, comprising:

forming, by an etching medium, at least one porous layer arranged at least partially between a first electrode and a second electrode of the semiconductor component so that the at least one porous layer is accessible for a medium acting from an outside on the semiconductor component and includes pores into which the medium is reachable at least partially; and providing the etching medium with at least one additive-wherein the additive at least one of reduces bubble formation, improves a wetting, and improves a drying.

14. The method of claim 13, wherein the additive includes an alcohol.

15. The method of claim 14, wherein the alcohol includes ethanol.

16. The method of claim 15, wherein the concentration of the ethanol is approximately 30% to approximately 90%.

17. A method for producing a semiconductor component, comprising:

forming, by an etching medium, at least one porous layer arranged at least partially between a first electrode and a second electrode of the semiconductor component so that the at least one porous layer is accessible for a medium acting from an outside on the semiconductor component and includes pores into which the medium is reachable at least partially wherein at least one of a measure of a porosity of the at least one porous layer and an extent of pores of the at least one porous layer is controlled by at least one of a current density of the etching medium, a concentration of hydrofluoric acid in the etching medium, one or more additives to the etching medium, a temperature, a doping, and a duration of the current flow.

* * * * *